(12) United States Patent
Kim et al.

(10) Patent No.: US 6,559,316 B2
(45) Date of Patent: May 6, 2003

(54) METHOD FOR PREPARING 2-(2-HYDROXYPHENYL)-2H-BENZOTRIAZOLE

(75) Inventors: Jeong-Kyu Kim, Daejeon-shi (KR); Chul-Hwan Choi, Daejeon-shi (KR)

(73) Assignee: LG Chem, Ltd., Seoul (KR)

(*) Notice: Subject to any disclaimer, the term of this patent is extended or adjusted under 35 U.S.C. 154(b) by 0 days.

(21) Appl. No.: 10/220,736

(22) PCT Filed: Jan. 15, 2002

(86) PCT No.: PCT/KR02/00062

§ 371 (c)(1),
(2), (4) Date: Sep. 5, 2002

(87) PCT Pub. No.: WO02/55508

PCT Pub. Date: Jul. 18, 2002

(65) Prior Publication Data

US 2003/0050480 A1 Mar. 13, 2003

(30) Foreign Application Priority Data

Jan. 15, 2001 (KR) .................... 2001-0002241

(51) Int. Cl.⁷ ............................... C07D 249/20
(52) U.S. Cl. ............................................. 548/260
(58) Field of Search ................................. 548/260

(56) References Cited

U.S. PATENT DOCUMENTS 3,983,132 A 9/1976 Strobel

FOREIGN PATENT DOCUMENTS

| EP | 0130938 A | 1/1985 |
| JP | 11 17871 A | 5/1989 |

*Primary Examiner*—Patricia L. Morris
(74) *Attorney, Agent, or Firm*—Birch, Stewart, Kolasch & Birch, LLP

(57) ABSTRACT

This invention provides a method for preparing 2-(2-hydroxyphenyl)-2H-benzotriatzole of formula (I) below, consisting of steps of: a) performing a first reduction in which hydrazine hydrate is added to a compound of formula (II) below with or without a phase transition catalyst in the presence of solvents which include a nonpolar solvent, water, and an alkaline compound, thereby preparing a compound of formula (III) below; and b) performing a second reduction in which water is added to the compound of formula (III) prepared in step a), and then zinc powder and sulfuric acid are added thereto with or without the phase transition catalyst, wherein, X is halogen or hydrogen; R is hydrogen, $C_1$–$C_{12}$ alkyl, $C_5$–$C_8$ cycloalkyl, phenyl, or phelyl-$C_1$–$C_4$ alkyl; and R' is $C_1$–$C_{12}$ alkyl, $C_5$–$C_8$ cycloalkyl, phenyl, or phenyl-C1–C4 alkyl.

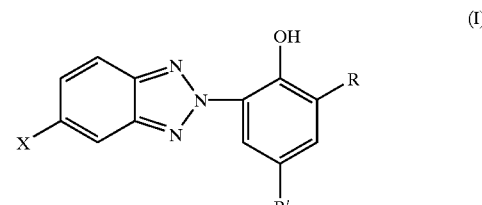

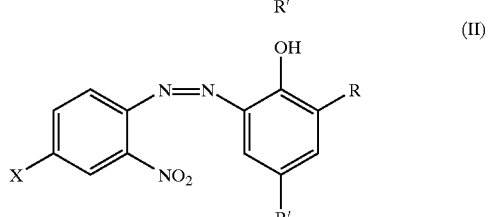

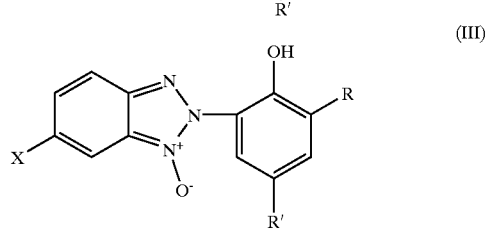

6 Claims, No Drawings

METHOD FOR PREPARING 2-(2-HYDROXYPHENYL)-2H-BENZOTRIAZOLE

This application is the national phase under 35 U.S.C. § 371 of PCT International Application No. PCT/KR02/00062 which has an International filing date of Jan. 15, 2002, which designated the United States of America.

BACKGROUND OF THE INVENTION (a) Field of the Invention

The present invention relates to a method for preparing 2-(2-hydroxyphenyl)-2H-benzotriazole, in which 2-(2-hydroxyphenyl)-2H-benzotriazole of formula (I) below can be prepared in a high yield and in an economical way.

(b) Description of the Related Art

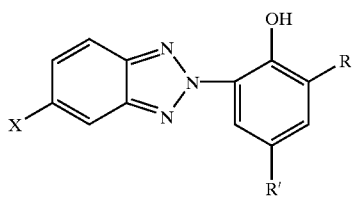

(I)

wherein X is halogen or hydrogen; R is hydrogen, $C_1$–$C_{12}$ alkyl, $C_5$–$C_8$ cycloalkyl, phenyl or phenyl-($C_1$–$C_4$) alkyl; and R' is $C_1$–$C_{12}$ alkyl, $C_5$–$C_8$ cycloalkyl, phenyl, or phenyl-($C_1$–$C_4$) alkyl.

Benzotriazole compounds are known in the art as ultraviolet absorbing agents useful for protection of organic polymeric substances from deterioration by ultraviolet irradiation. In general, various methods are known to obtain the benzotriazole by reducing a compound of formula (II) used as a starting reagent via an intermediate product of formula (III).

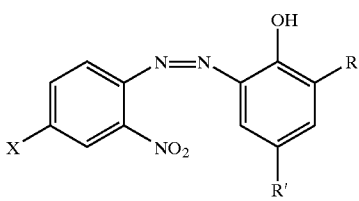

(II)

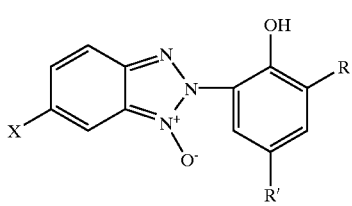

(III)

wherein, X is halogen or hydrogen; R is hydrogen $C_1$–$C_{12}$ alkyl, $C_5$–$C_8$ cycloalkyl, phenyl or phenyl-($C_1$–$C_4$) alkyl; and R' is $C_1$–$C_{12}$ alkyl, $C_5$–$C_8$ cycloalkyl, phenyl, or phenyl-($C_1$–$C_4$) alkyl.

Among the known processes, a method in which hydrazine is used as a reducing agent has an advantage in that it allows the reaction to be carried out under atmospheric pressure (U.S. Pat. No. 4,001,266, Ger. Often. DE 2,454, 889, Fr Demande FR 2,292,708), but it also has disadvantages in that expensive ethers such as diethylene glycol diethyl or dimethyl ether are used as solvents, and that the reaction temperature is at least 100° C. (in the Examples of the present invention; at least 130° C.), thereby a side-reaction takes place to form large amounts of byproducts. Moreover, reaction time is prolonged in order to distill off water that is present in the reagents, and during distillation by heating of the reactants, there is even a potential danger of explosion due to the property of ether as a solvent that it can easily produce peroxid compounds.

The intermediate product that is denoted by the formula (III) can be synthesized by a reaction of a derivative having the formula (II) with zinc powder in the presence of low alcohol or water (Japan Kokai JP 53,063,379), and in such a case, since an excessive amount of zinc (4 equivalents) and alkali metals (4 equivalents) are used, post treatment of large amounts of zinc product is required and cost of waste treatment is increased for the neutralization of the excessive amount of alkali metals.

Alternatively, there is an example of using hydrazine and zinc as reducing agents and an alcohol as a solvent, but, in this case, for the preparation of an N-oxide compound having the formula (III), the solvent has to be changed to chlorobenzene after crystallization and filtration. Consequently, there are drawbacks in that a large numbers of equipments are needed and the complicated process causes an extension of the processing period, and furthermore, there can be a product loss through the filtrate during filtration as well as other problems such as additional cost for the solvent recovery.

SUMMARY OF THE INVENTION

In consideration of the abovementioned problems, it is an object of the present invention to provide a method for preparing 2-(2-hydroxyphenyl)-2H-benzotriazole of the formula (I) above in an economical way and with a high yield by simplifying solvents used.

In order to achieve the object of the present invention, there is provided a method for preparing 2-(2-hydroxyphenyl)-2H-benzotriazole of formula (I) below, comprising steps of:

a) performing a first reduction in which hydrazine hydrate is added to a compound of formula (II) below with or without a phase transition catalyst in the presence of solvents which include a nonpolar solvent, water, and an alkaline compound, thereby preparing a compound of formula (III) below; and b) performing a second reduction in which water is added to the compound of formula (III) prepared in step a), and then zinc powder and sulfuric acid are added thereto with or without the phase transition catalyst:

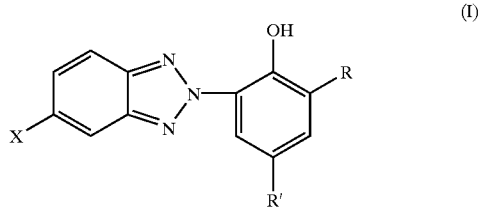

(I)

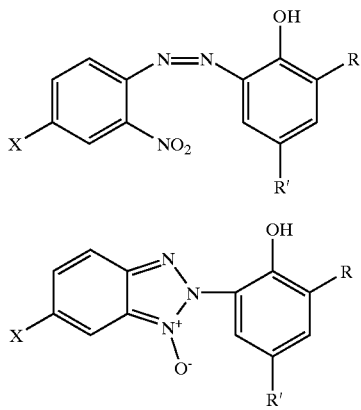

wherein, X is halogen or hydrogen; R is hydrogen, $C_1$–$C_{12}$ alkyl, $C_5$–$C_8$ cycloalkyl, phenyl, or phenyl-$C_1$–$C_4$ alkyl; and R' is $C_1$–$C_{12}$ alkyl, $C_5$–$C_8$ cycloalkyl, phenyl, or phenyl-$C_1$–$C_4$ alkyl.

DETAILED DESCRIPTION OF THE PREFERRED EMBODIMENTS

The present invention will be described in detail below.

The present invention relates to a method for preparing 2-(2-hydroxyphenyl)-2H-benzotriazole, in which an intermediate product having the formula (III) is prepared by addition of hydrazine hydrate as a reducing agent to an o-nitrophenylazohydroxyphenyl compound having the formula (II) using reaction solvents including water and a nonpolar solvent that is available at a low price, then without performing an isolation or additional purification process, a second reduction is performed in the presence of a base or an acid by adding only water to the intermediate product obtained above and by using zinc powder as an reducing agent. According to the present invention, in the first reduction only a nonpolar solvent mixed with water is used as a solvent, and in the second reduction only water is added without using any further organic solvent, so that the process is simplified and the possibility of product loss due to the solvent replacement can be avoided, which furnishes the process with economic efficiency.

Examples of a preferred compound of formula (I) according to the invention include:

2-(2-hydroxy-5-methylphenyl)-2H-benzotriazole, 2-(2-hydroxy-3-tert-butyl-5-methylphenyl)-5-chloro-2H-benzotriazole, 2-(2-hydroxy3tert-di-amyl-5-methylphenyl)-2H-benzotriazole, 2-(2-hydroxy-5-tert-octyllphenyl)-2H-benzotriazole, 2-(2-hydroxy-3-5-bis-α,α-dimethylberhzylphenyl)-2H-benzotriazole, and 2-(2-hydroxy-3-5-di-tert-butylphenyl)-2H-benzotriazole.

In the present invention, the benzotriazole of formula (I) is prepared through reduction in two steps as described in the following.

The starting material used in the present invention is an o-nitrophenylazohydroxyphenyl compound of formula (II), and it is supplied to a reactor together with a base, and then a nonpolar solvent and water are added thereto. Subsequently, a first reduction is performed to obtain an intermediate product of formula (III) through a procedure in which hydrazine hydrate as a reducing agent is added dropwise while maintaining a temperature of 50° to 140° C., preferably of 60° to 100° C., to proceed the reaction, and thereafter completion of the reaction is confirmed by means of high performance liquid chromatography (HPLC).

The nonpolar solvent is preferably at least one selected from the group consisting of o-, m-, and p-xylene, ethylbenzene, toluene, and benzene.

The base is preferably an alkali metal salt, and a more specific example of the alkali metal salt is sodium hydroxide or potassium hydroxide.

In this process, the reaction may be performed either under the presence of or without a phase transition catalyst, and in the case of using the phase transition catalyst the reaction rate is accelerated. The phase transition catalyst is preferably at least one selected from the group consisting of tetraethylbenzyl ammonium chloride, tetrabutyl ammonium chloride, tetrabutyl ammonium bromide, hydroquinone, anthraquinone, and catechol.

The hydrazine hydrate used as a reducing agent is added in an amount of 0.5 to 0.7 mol equivalent by dropping, and the duration of the first reduction is a few minutes to a few hours, and normally it takes about ½ to 4 hours.

Subsequently, when the first reduction is completed, benzotriazole of formula (I) is prepared by means of a second reduction performed as described below.

The intermediate product of formula (III) is neutralized with sulfuric acid or hydrochloric acid, then an aqueous layer is removed therefrom and the organic layer is washed with water in order to remove trace amounts of mineral acid. Additional water is added to the organic layer from which the aqueous layer is removed, and then 1 mol to 1.3 mol equivalent of zinc powder as a reducing agent is added at one time, followed by dropwise addition of 1 mol to 2 mol equivalent of sulfuric acid at a temperature of 50° to 100° C., and after ½ to 3 hours of reaction the second reduction is completed. In this process, the sequence of adding zinc powder and sulfuric acid may be reversed with the same result.

When the second reduction is completed, agitation is stopped and the aqueous layer in the lower part, which contains zinc sulfate, is removed. After removing unreacted zinc by filtration, the filtrate is decolored by a decoloring agent and then dried to give benzotriazole of formula (I) with high purity.

As described above, in the conventional reduction process for producing benzotriazole, the reaction is performed by using an excessive amount of zinc (4 equivalents) and alkali metals (4 equivalents) in the presence of low alcohol or water, so that post-treatment of a large amount of byproduct is required and waste treatment cost for the neutralization of the excessive amount of alkali metals is increased. Moreover, it requires further steps of crystallization, filtration, and purification in order to replace the solvents, thus resulting in the loss of product through filtrate. According to the present invention, however, a nonpolar solvent as the sole solvent is used for the reduction, and therefore a relatively small amount of zinc (1 to 1.3 equivalents) and alkali metal (1 to 2 equivalents) is used, and no further process is required for isolating or purifying of impurities in the intermediate product, and thus with a smaller amount of metallic reducing agent it is possible to produce benzotriazole in a high yield and achieve economic efficiency.

The present invention will be illustrated in further detail with reference of the following examples, but the present invention is not limited thereto.

EXAMPLES

Example 1

Preparation of 2-(2-Hydroxy-5-methylphenyl)-2H-benzotriazole 144 g of 2-nitro-2-hydroxy-5-methylazobenzene (89.1%), 80 g of sodium hydroxide (50%), 190 g of o-xylene, and water were charged into a 500 ml reactor and 18.8 g of hydrazine hydrate (80%) as a reducing agent were slowly added dropwise over 30 minutes while maintaining the temperature at 60° to 80° C.

After 2 hours of agitation, the reaction was completed, and then an analysis with HPLC was carried out. The completion of the first reduction could be confirmed from the fact that 2-nitro-2-hydroxy-5-methylazobenzene used as a starting material had vanished, and 2-(2-hydroxy-5-methylphenyl)-2H-benzotriazole-N-oxide was produced. After the reactants were neutralized with sulfuric acid, a water layer in the lower part was removed by separation and the remainder was washed with water.

Subsequently, 190 g of water and 42.6 g of zinc powder (96%) were added to the resultant solution, and then a second reduction was carried out by dropwise addition of 77 g of sulfuric acid (95%) over 30 minutes while maintaining the temperature at 60° to 80° C. The reaction was completed after stirring the reactants for 2 hours, and then unreacted zinc powder was removed by filtration and the water layer in the lower part was removed by separation. Coloring materials in the resultant organic layer were removed by extraction with sulfuric acid, and after decoloring of the solution with a decoloring agent, crystallization was performed by addition of 300 g of methanol.

The obtained solid mass was washed and dried to yield 98.7 g of 2-(2-hydroxy-5-methylphenyl)-2H-benzotriazole (88% of theoretical yield) with high purity, and an additional 5.6 g (5% of theoretical yield) of the product were obtained from the extract with sulfuric acid and from the filtrate.

Example 2

The same process as in Example 1 was carried out except that, after the first reduction, 77 g of sulfuric acid (95%) were charged beforehand and then 42.6 g of zinc powder (96%) were added portionwise. The result was that almost the same yield of 2-(2-hydroxy-5-methylphenyl)-2H-benzotriazole as that of Example 1 was attained.

Example 3

Preparation of 2-(2-Hydroxy-3-tert-butyl-5-methylphenyl)-5-chloro-2H-benzotriazole 173 g of 2-nitro-4-chloro-2-hydroxy-3-tert-butyl-5-methylazobenzene (77.4%), 46 g of sodium hydroxide (50%), hydroquinone, 207 g of o-xylene as a solvent, and 104 g of water were charged into a 1000 ml reactor and 15.5 g of hydrazine hydrate (80%) as a reducing agent were slowly added dropwise over 40 minutes while maintaining the temperature at 70° to 96° C.

After 4 hours of agitation, the reaction was completed, and then an analysis with HPLC was carried out. The completion of the first reduction could be confirmed from the fact that 2-nitro-4-chloro-2-hydroxy-3-tert-butyl-5-methylazobenzene used as a starting material had vanished, and 2-(2-hydroxy-3-tert-butyl-5-methylphenyl)-5-chloro-2H-benzotriazole-N-oxide was produced. After the reactants were neutralized with sulfuric acid, a water layer in the lower part was removed by separation, and the remainder was washed with water.

Subsequently, 207 g of water and 34 g of zinc powder (96%) were added to the resultant solution, and then a second reduction was carried out by adding 63 g of sulfuric acid (95%) dropwise over 40 minutes while maintaining the temperature at 60° to 80° C. The reaction was completed after stirring the reactants for 1 hour, and then unreacted zinc powder was removed by filtration and a water layer in the lower part was removed by separation. Coloring materials in the resultant organic layer were removed by extraction with sulfuric acid, and after decoloring of the solution with a decoloring agent, crystallization was performed by addition of 400 g of methanol.

The obtained solid mass was washed and dried to yield 86.6 g of 2-(2-hydroxy-3-tert-butyl-5-methylphenyl)-5-chloro-2H-benzotriazole (87% of theoretical yield) with high purity, and an additional 3.4 g (3% of theoretical yield) of the product were obtained from the extract with sulfuric acid and from the filtrate.

Example 4

The same process as in Example 3 was carried out except that, after the first reduction, 63 g of sulfuric acid (95%) were charged beforehand and then 34 g of zinc powder (96%) were added portionwise. The result was that almost the same yield of 2-(2-hydroxy-3-tert-butyl-5-methylphenyl)-5-chloro-2H-benzotriazole as that of Example 3 was attained.

Example 5

The same process as in Example 3 was carried out except that instead of hydroquinone, tetrabutyl ammonium chloride was used as the catalyst in the first reduction, and tetraammonium chloride was used as the catalyst in the second reduction. The result was that reaction time of the first reduction was shortened from 4 hours to 2 hours, and the reaction time of the second reduction was shortened to 1 hour. In addition, the yield of 2-(2-hydroxy-3-tert-butyl-5-methylphenyl)-5-chloro-2H-benzotriazole was almost the same as that of Example 3.

Example 6

Preparation of 2-(2-Hydroxy-3-tert-butyl-5-methylphenyl)-5-chloro-2H-benzotriazole 161 g of 2-nitro-4-chloro-2-hydroxy-3-5-di-tert-butyl-azobenzene (69.2%), 34 g of sodium hydroxide (50%), hydroquinone, 174 g of o-xylene as a solvent, and 174 g of water were charged into a 500 ml reactor, and 10.7 g of hydrazine hydrate (80%) as a reducing agent were slowly added dropwise over 40 minutes while maintaining the temperature at 70° to 96° C.

After 4 hours of agitation, the reaction was completed, and then an analysis with HPLC was carried out. The completion of the first reduction could be confirmed from the fact that 2-nitro-4-chloro-2-hydroxy-3-5-di-tert-butyl-azobenzene used as a starting material had vanished, and 2-(2-hydroxy-3-tert-butyl-5-methylphenyl)-5-chloro-2H-benzotriazole-N-oxide was produced. After the reactants were neutralized with sulfuric acid, the water layer in the lower part was removed by separation and the remainder was washed with water.

Subsequently, 174 g of water and 23.3 g of zinc powder (96%) were added to the resultant solution, and then a second reduction was carried out by adding 44 g of sulfuric acid (95%) dropwise over 30 minutes while maintaining the temperature at 60° to 80° C. The reaction was completed after stirring the reactants for 2 hours, and then unreacted zinc powder was removed by filtration and the water layer in the lower part was removed by separation. Coloring materials in the resultant organic layer were removed by extraction with sulfuric acid, and after decoloring of the solution with a decoloring agent, crystallization was performed by addition of 400 g of methanol.

The obtained solid mass was washed and dried to yield 88.0 g of 2-(2-hydroxy-3-tert-butyl-5-methylphenyl)-5-chloro-2H-benzotriazole (86% of theoretical yield) with high purity, and an additional 3.1 g (3% of theoretical yield) of the product were obtained from the extract with sulfuric acid and from the filtrate.

Example 7

The same process as in Example 6 was carried out except that the sequence of addition of sulfuric acid and zinc powder in the second reduction was reversed. The result was that almost the same yield of 2-(2-hydroxy-3-tert-butyl-5-methylphenyl)-5-chloro-2H-benzotriazole as that of Example 6 was attained.

Example 8

The same process as in Example 6 was carried out except that tetraammonium chloride was used as the catalyst in both the first and the second reduction. The result was that the same yield of 2-(2-hydroxy-3-tert-butyl-5-methylphenyl)-5-chloro-2H-benzotriazole as that of Example 6 was attained. In this case, reaction time of the first reduction was shortened to 1.5 hours and the reaction time of the second reduction was shortened to 1 hour.

Example 9

Preparation of 2-(2-Hydroxy-3-tert-di-amyl-5-methylphenyl)-2H-benzotriazole 95 g of 2-nitro-2-hydroxy-3-5-di-tert-amyl-azobenzene (85.3%), 34 g of sodium hydroxide (50%), hydroquinone, 127 g of o-xylene as a solvent, and 127 g of water were charged into a 500 ml reactor and 8.0 g of hydrazine hydrate (80%) as a reducing agent were slowly added dropwise over 20 minutes while maintaining the temperature at 70° to 105° C.

After 4 hours of agitation, the reaction was completed, and then an analysis with HPLC was carried out. The completion of the first reduction could be confirmed from the fact that hydroxy-5-azobenzene used as a starting material had vanished and 2-(2-hydroxy-3-5-di-tert-amylphenyl)-2H-benzotriazole-N-oxide was produced. After the reactants were neutralized with sulfuric acid, the water layer in the lower part was removed by separation, and the remainder was washed with water.

Subsequently, 207 g of water and 34 g of zinc powder (96%) were added to the resultant solution, and then a second reduction was carried out by adding 63 g of sulfuric acid (95%) dropwise over 40 minutes while maintaining the temperature at 60° to 80° C. The reaction was completed after stirring the reactants for 2 hours, and then unreacted zinc powder was removed by filtration and the water layer in the lower part was removed by separation. Coloring materials in the resultant organic layer were removed by extraction with sulfuric acid and after decoloring of the solution with a decoloring agent, crystallization was performed by addition of 400 g of methanol.

The obtained solid mass was washed and dried to yield 88.6 g of 2-(2-hydroxy-3-tert-di-amny-5-methylphenyl)-5-chloro-2H-benzotriazole (86% of theoretical yield) with high purity, and an additional 3.1 g (3% of theoretical yield) of the product were obtained from the extract with is sulfuric acid and from the filtrate.

Example 10

The same process as in Example 9 was carried out except that the sequence of addition of sulfuric acid and zinc powder in the second reduction was reversed. The result was that almost the same yield of 2-(2-hydroxy-3-tert-di-amyl-5-methylphenyt)-2H-benzotriazole as that of Example 9 was attained.

Example 11

The same process as in Example 9 was carried out except that tetraammonium chloride was used as the catalyst in both the first and the second reduction. The result was that the same yield of 2-(2-hydroxy-3-tert-di-amyl-5-methylphenyl)-2H-benzotriazole as that of Example 9 was attained. In this case, reaction time of the first reduction was shortened to 1.5 hours and the reaction time of the second reduction was shortened to 1 hour.

Example 12

Preparation of 2-(2-Hydroxy-5-tert-octylphenyl)-2H-benzotriazole

The same process as in Example 1 was carried out except that 2-nitro-2-hydrozy-5-tert-octyl-azobenzene (91%) was used as a starting material. The result was that the yield of 2-(2-hydroxy-5-tert-octylphenyl)-2H-benzotriazole was 93% of theoretical yield.

Example 13

The same process as in Example 12 was carried out except that the sequence of addition of sulfuric acid and zinc powder in the second reduction was reversed. The result was that almost the same yield of 2-(2-hydroxy-5-tert-octylphenyl)-2H-benzotriazole as that of Example 12 was attained.

Example 14

The same process as in Example 12 was carried out except that tetraammonium chloride was used as the catalyst in both the first and the second reduction. The result was that the same yield of 2-(2-hydroxy-5-tert-octyllphenyl)-2H-benzotriazole as that of Example 12 was attained. In this case, reaction time of the first reduction was shortened to 1.5 hours and the reaction time of the second reduction was shortened to 1 hour.

Example 15

Preparation of 2-(2-Hydroxy-3-5-bis-α,α-dimethylbenzylphenyl)-2H-benzotriazole

The same process as in Example 3 was carried out except that 2-nitro-2-hydrozy-3-5-bis-a,a-dimethylbenzylazobenzene (84.1%) was used as a starting material. The result was that the yield of 2-(2-hydroxy-3-5-bis-α,α-dimethylbenzylphenyl)-2H-benzotriazole was 93% of theoretical yield.

Example 16

The same process as in Example 15 was carried out except that the sequence of addition of sulfuric acid and zinc powder in the second reduction was reversed. The result was that almost the same yield of 2-(2-hydroxy-3-5-bis-α,α-dimethylbenzylphenyl)-2H-benzotriazole as that of Example 15 was attained.

Example 17

The same process as in Example 15 was carried out except that tetraammonium chloride was used as the catalyst in both the first and the second reduction. The result was that the same yield of 2-(2-hydroxy-3-5-bis-α,α-dimethylbenzylphenyl)-2H-benzotriazole as that of Example 15 was attained. In this case, reaction time of the first reduction was shortened to 1.5 hours and the reaction time of the second reduction was shortened to 1 hour.

Example 18

Preparation of 2-(2-Hydroxy-3-5-di-tert-butylphenyl)-2H-benzotriazole

The same process as in Example 3 was carried out except that 2-nitro-2-hydrozy-3-5-di-tert-butylazobenzene (89%) was used as a starting material. The result was that the yield of 2-(2-hydroxy-3-5-di-tert-butylphenyl)-2H-benzotriazole was 92% of theoretical yield.

Example 19

The same process as in Example 18 was carried out except that the sequence of addition of sulfuric acid and zinc powder in the second reduction was reversed. The result was that almost the same yield of 2-(2-hydroxy-3-5-di-tert-butylphenyl)-2H-benzotriazole as that of Example 18 was attained.

Example 20

The same process as in Example 18 was carried out except that tetraammonium chloride was used as the catalyst in both the first and the second reduction. The result was that the same yield of 2-(2-hydroxy-3-5-di-tert-butylphenyl)-2H-benzotriazole as that of Example 18 was attained. In this case, reaction time of the first reduction was shortened to 1.5 hours and the reaction time of the second reduction was shortened to 1 hour.

As described above, the method for preparing benzotriazole according to the present invention is characterized in that the first reduction is carried out using only nonpolar solvent as a solvent and the second reduction is carried out directly onto an intermediate product without an extra purification or separation process, so that the process is simplified and product loss due to solvent replacement can be avoided, and thereby the final product can be prepared economically at a high yield.

What is claimed is:

1. A method for preparing 2-(2-hydroxyphenyl)-2H-benzotriazole of formula (I) below, comprising steps of:

a) performing a first reduction in which hydrazine hydrate is added to a compound of formula (II) below with or without a phase transition catalyst in the presence of solvents which include a nonpolar solvent, water, and an alkaline compound, thereby preparing a compound of formula (III) below; and b) performing a second reduction in which water is added to the compound of formula (III) prepared in step a), and then zinc powder and sulfuric acid are added thereto with or without the phase transition catalyst:

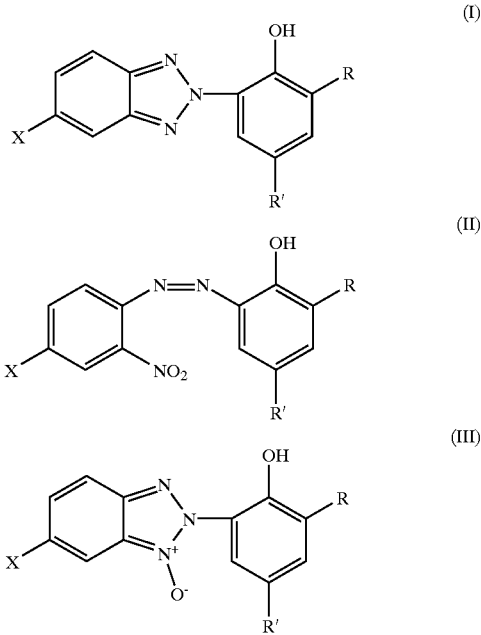

wherein, X is halogen or hydrogen; R is hydrogen, $C_1$–$C_{12}$ alkyl, $C_5$–$C_8$ cycloalkyl, phenyl, or phenyl-$C_1$–$C_4$ alkyl; and R' is $C_1$–$C_{12}$ alkyl, $C_5$–$C_8$ cycloalkyl, phenyl, or phenyl-$C_1$–$C_4$ alkyl.

2. The method according to claim 1, wherein the nonpolar solvent used in step a) is at least one selected from the group consisting of o-, m-, p-xylene, mixtures thereof, ethylbenzene, toluene, and benzene.

3. The method according to claim 1, wherein the phase transition catalyst used in both step a) and step b) is at least one selected from the group consisting of tetraethylbenzyl ammonium chloride, tetrabutyl ammonium chloride, tetrabutyl ammonium bromide, hydroquinone, anthraquinone, and catechol.

4. The method according to claim 1, wherein an equivalent of hydrazine hydrate used in step a) is 0.5 to 0.7 mol.

5. The method according to claim 1, wherein an equivalent of zinc powder used in step b) is 1 to 1.3 mol.

6. The method according to claim 1, wherein an equivalent of sulfuric acid used in step b) is 1 to 2 mol.

* * * * *